US007031430B2

(12) United States Patent
Kaucic, Jr. et al.

(10) Patent No.: US 7,031,430 B2
(45) Date of Patent: Apr. 18, 2006

(54) SYSTEM AND METHOD FOR DETECTING OBJECTS WITH DIFFERENTIAL OPERATORS

(75) Inventors: Robert August Kaucic, Jr., Niskayuna, NY (US); Ricardo Scott Avila, Clifton Park, NY (US); Timothy Patrick Kelliher, Scotia, NY (US); Daniel James Blezek, Niskayuna, NY (US); William MaComber Leue, Albany, NY (US)

(73) Assignee: General Electric Company, Niskayuna, NY (US)

( * ) Notice: Subject to any disclaimer, the term of this patent is extended or adjusted under 35 U.S.C. 154(b) by 98 days.

(21) Appl. No.: 10/818,049

(22) Filed: Apr. 6, 2004

(65) Prior Publication Data

US 2005/0226360 A1  Oct. 13, 2005

(51) Int. Cl.
*G01N 23/04* (2006.01)
(52) U.S. Cl. .............................. 378/57; 378/8; 378/901
(58) Field of Classification Search ............... 378/4, 378/8, 15, 57, 901; 382/131
See application file for complete search history.

(56) References Cited

U.S. PATENT DOCUMENTS

| 3,432,664 | A | 3/1969 | Robison |
| 3,518,433 | A | 6/1970 | Owen |
| 3,714,486 | A | 1/1973 | McCrary |
| 3,783,288 | A | 1/1974 | Barbour et al. |
| 4,200,800 | A | 4/1980 | Swift |
| 4,289,969 | A | 9/1981 | Cooperstein et al. |
| 5,115,394 | A | 5/1992 | Walters |
| 5,200,626 | A | 4/1993 | Schultz et al. |
| 5,247,561 | A | 9/1993 | Kotowski |
| 5,491,734 | A | 2/1996 | Boyd et al. |
| 5,784,481 | A | 7/1998 | Hu |
| 6,115,448 | A | 9/2000 | Hoffman |
| 6,207,958 | B1 | 3/2001 | Giakos |
| 6,385,292 | B1 | 5/2002 | Dunham et al. |
| 6,418,189 | B1 | 7/2002 | Schafer |

(Continued)

FOREIGN PATENT DOCUMENTS

EP        1230950 B1      9/2002

(Continued)

OTHER PUBLICATIONS

"Three-Dimensional Multi-Scale Line Filter for Segmentation and Visualization of Curvilinear Structures in Medical Images," Y. Sato et al., Medical Image Analysis (1998) vol. 2, No. 2, pp. 143-168.

(Continued)

*Primary Examiner*—David V Bruce
(74) *Attorney, Agent, or Firm*—William E. Powell, III; Christian G. Cabou

(57) ABSTRACT

A system and a method for detecting an object, such as an explosive device or material, located within a closed article, such as a piece of luggage or a parcel. The system includes an acquisition subsystem for acquiring information pertaining to a specific object, a reconstruction subsystem for reconstructing acquired information pertaining to the specific object into image data, and a computer-aided detection subsystem adapted for identifying the specific object through the use of differential operators. The method includes obtaining image data of the one object, computing a differential operator for each voxel of the image data, computing eigenvalues and eigenvectors for each of the voxels, and computing a scalar function of the eigenvalues to ascertain whether each of the voxels represents a portion of the one object.

45 Claims, 3 Drawing Sheets

U.S. PATENT DOCUMENTS

| | | |
|---|---|---|
| 6,574,299 B1 | 6/2003 | Katsevich |
| 6,937,776 B1 * | 8/2005 | Li et al. .................... 382/260 |
| 2002/0085674 A1 | 7/2002 | Price et al. |
| 2003/0072407 A1 | 4/2003 | Mihara et al. |
| 2004/0151356 A1 * | 8/2004 | Li et al. .................... 382/131 |

FOREIGN PATENT DOCUMENTS

| | | |
|---|---|---|
| EP | 1277439 | 1/2003 |
| GB | 1390575 | 4/1975 |
| WO | 99/67806 | 6/1998 |

OTHER PUBLICATIONS

"Three-Dimensional Multi-Scale Line Filter for Segmentation and Visualization of Curvilinear Structures in Medical Images," Y. Sato et al.. Medical Image Analysis (1998) vol. 2, No. 2, pp. 143-168.

* cited by examiner

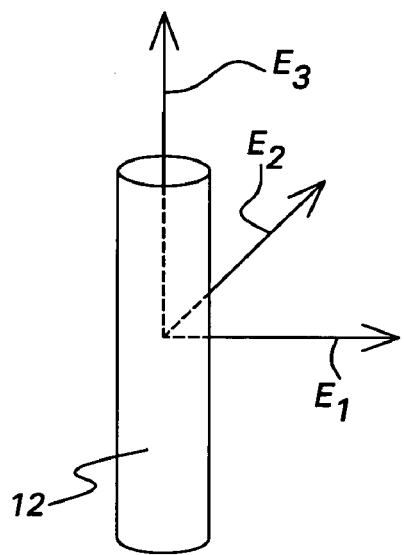
FIG.3
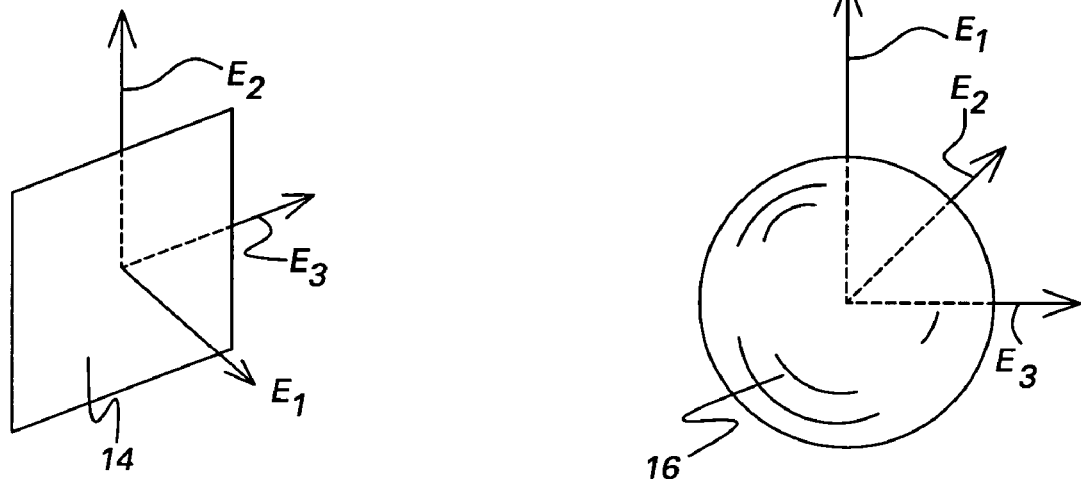
FIG.4
FIG.5
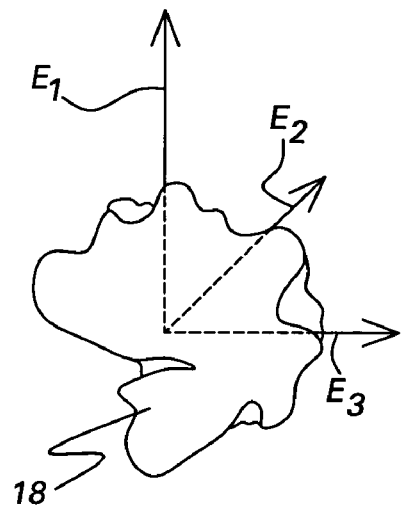
FIG.6

SYSTEM AND METHOD FOR DETECTING
OBJECTS WITH DIFFERENTIAL
OPERATORS

BACKGROUND

The invention relates generally to a system and a method for detecting and segmenting objects, and more particularly to a system and a method for detecting the identity of an object within an enclosed article and segmenting that object from surrounding objects.

There continues to be, a demand for heightened security surrounding various communication and transportation venues. For example, metal detectors and x-ray machines are standard security devices employed at airports for screening passengers and their carry-on and checked luggage. The United States Postal Service also employs x-ray technology for screening parcels.

The capability for automatically screening a high-throughput of luggage in an efficient and cost-effective manner is currently insufficient. The screening systems currently in place record false positives at rates higher than desirable. The high number of false positives forces alternative follow-on inspections, such as trace detection or manual inspection of the luggage, thereby increasing the average screening time per bag substantially.

Certain types of contraband offer unique problems for detection. For example, sheet-like explosive material within an enclosed article, such as luggage, is difficult to detect due to its physical characteristics. Further, differentiation of one object from another at the rapid pace necessary for screening a high-throughput of luggage is needed for the ability to quickly detect contraband. There is a need for a detection mechanism for detecting and segmenting certain contraband materials from other non-contraband objects located within an enclosed article, such as luggage.

BRIEF DESCRIPTION OF THE DRAWINGS

FIG. 3 illustrates eigenvectors for a cylinder computed by an AED stage of the system of FIG. 1.

FIG. 4 illustrates eigenvectors in three-axes for a sheet-like material computed by an AED stage of the system of FIG. 1.

FIG. 5 illustrates eigenvectors in three-axes for a sphere computed by an AED stage of the system of FIG. 1.

FIG. 6 illustrates eigenvectors in three-axes for a blob-like material computed by an AED stage of the system of FIG. 1.

SUMMARY

Figure 1:
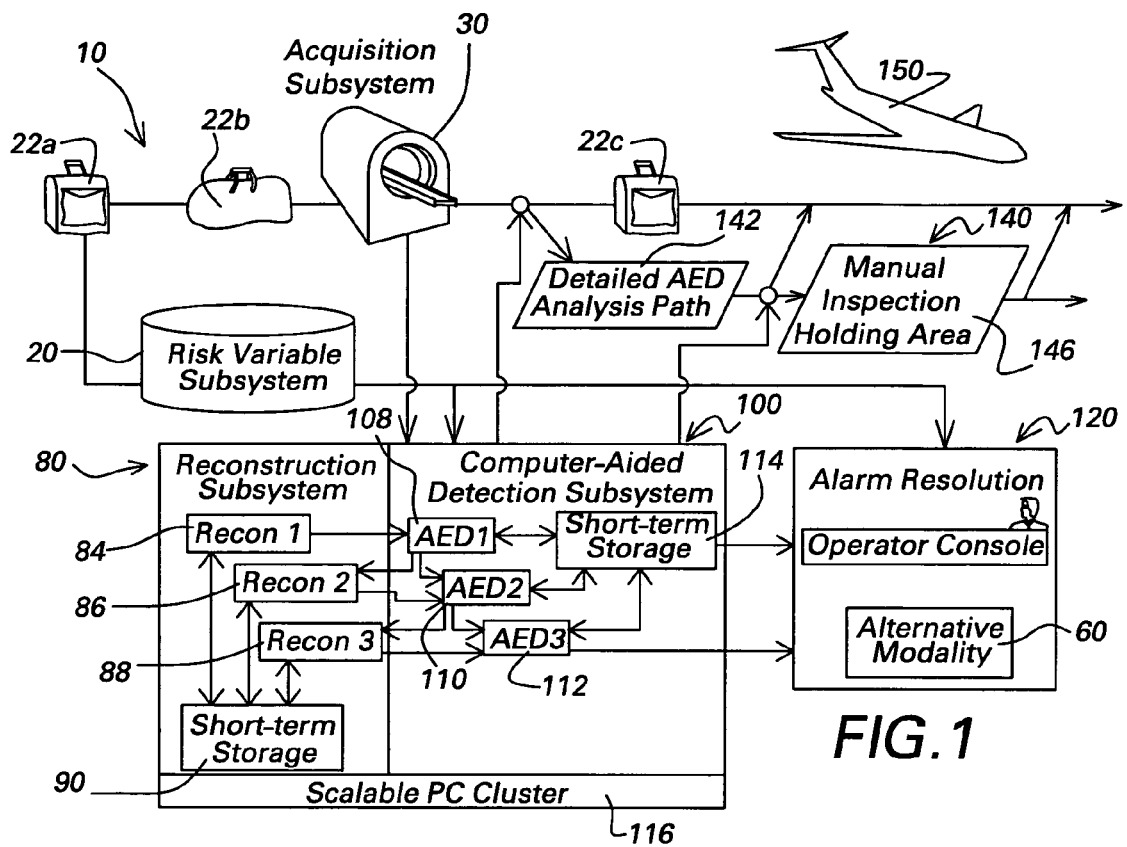
FIG. 1 is a perspective schematic view of an object detecting system in accordance with an embodiment of the invention.

The present invention describes a system and a method for detecting an object, such as an explosive device or material, located within a closed article, such as a piece of luggage or a parcel. Such methods can also be used to detect objects inside an animal or human body, such as vascular structure and nodules.

One aspect of the invention is a system for distinguishing a specific object from other objects residing within an enclosed container. The system includes an acquisition subsystem for acquiring information pertaining to a specific object, a reconstruction subsystem for reconstructing acquired information pertaining to the specific object into image data, and a computer-aided detection subsystem adapted for identifying the specific object through differential operators.

Another aspect of the invention is a system for distinguishing a specific object from other objects residing within an enclosed container. The system includes a computed tomography machine for acquiring information pertaining to a specific object, a reconstruction subsystem for reconstructing acquired information pertaining to the specific object into image data, and a computer-aided detection subsystem adapted for identifying the specific object through differential operators. The computer-aided detection subsystem comprises more than one stage.

Another aspect of the invention is a system for identifying a specific object from other objects resident within an enclosed container. The system includes an acquisition subsystem for acquiring information pertaining to a specific object, a reconstruction subsystem for reconstructing acquired information pertaining to the specific object into image data, and a means for identifying the specific object through the use of differential operators. Vectors derived from the differential operators are used in the identification of the specific object.

Another aspect of the invention is a method for distinguishing a specific object from other objects within an enclosed container. The method includes the steps of obtaining image data of the a specific object, computing a differential operator for each voxel of the image data, computing eigenvalues and eigenvectors for each of the voxels, and computing a scalar function of the eigenvalues to ascertain whether each of the voxels represents a portion of the specific object.

Another aspect of the invention is a method for distinguishing one locally sheet-like object from other objects within an enclosed container. The method includes the steps of obtaining image data of a locally sheet-like object, computing a differential operator for each voxel of the image data with at least one stage of a computer-aided detection subsystem, computing eigenvalues and eigenvectors for each of the voxels, and computing a scalar function of the eigenvalues to ascertain whether each of the voxels represents a portion of the locally sheet-like object. The scalar function responds to a greater degree to locally sheet-like materials than to materials having other geometries.

These and other advantages and features will be more readily understood from the following detailed description of preferred embodiments of the invention that is provided in connection with the accompanying drawings.

DETAILED DESCRIPTION OF PREFERRED EMBODIMENTS

An object detecting system 10 is shown in FIG. 1. The illustrated system 10 includes a variety of subsystems, some of which are optional and may be omitted from the system 10. As shown, the system 10 includes a risk variable subsystem 20, an acquisition subsystem 30, an alternative modality subsystem 60, a reconstruction subsystem 80, an identifying means, such as a computer-aided detection (CAD) subsystem 100, and an alarm resolution subsystem 120. The object detecting system 10 is adapted to accommodate a high throughput of articles, for example, screening of upwards of one thousand individual pieces of checked luggage within a one hour time period, in an expeditious manner with a high detection rate and a tolerable number of false positives. The CAD subsystem 100 utilizes differential operators to distinguish one object from another. Details regarding the risk variable subsystem 20, the acquisition subsystem 30, the alternative modality subsystem 60, and the alarm resolution subsystem 120 are found in U.S. patent application Ser. No. 10/737,887, filed Dec. 15, 2003, the entire contents of which are hereby incorporated by reference.

The illustrated acquisition subsystem 30 may include a computed tomography (CT) scanner. Suitable CT scanners include "third generation" computed tomography (CT) scanners, 4$^{th}$ generation CT scanners (commercially available from American Science and Engineering, Inc.), 5$^{th}$ generation CT scanners (commercially available under the trademark IMATRON® by Imatron Inc.), and CT scanners including a stationary x-ray source and a stationary detector. The view data generated by the acquisition subsystem 30 is communicated to the reconstruction subsystem 80 or the CAD subsystem 100.

The view data is received by the reconstruction subsystem 80 from the acquisition subsystem 30. The reconstruction subsystem 80 includes a plurality of reconstruction stages 84, 86, each of which includes one or more algorithms for reconstructing the view data. Short-term storage 90 is included within the reconstruction subsystem 80 and is in communication with each of the reconstruction stages 84, 86. The reconstruction subsystem 80 functions to reconstruct the view data received from the acquisition subsystem 30 into image data, which can then be communicated to the CAD subsystem 100 for further analysis.

The illustrated CAD subsystem 100 is in connection with a node 24 within the transportation line that transports luggage 22a, 22b, and 22c (hereinafter referred to as luggage 22n) toward an aircraft 150. The node 24 is a decision point at which, based upon information obtained through the CAD subsystem 100, one or more pieces of luggage 22n are shunted out of line to the aircraft 150 and to a manual inspection subsystem 140 including an alarm resolution area 142 and a manual inspection holding area 146.

The CAD subsystem 100 includes a plurality of automated explosive detection (AED) stages 108, 110, 112, which are in communication with the reconstruction stages 84, 86. As illustrated in FIG. 1, for example, the reconstruction stage 84 is in communication with the AED stage 108, which in turn is in communication with the AED stage 110 and the short-term storage 114. The AED stage 110 is in communication with both the short-term storage 114 and the AED stage 112. The reconstruction stage 86 is in communication with the short-term storage 90 and the AED stage 112. A scalable cluster of personal computers 116, potentially augmented with Field Programmable Gate Arrays (FPGA) or Application Specific Integrated Circuits (ASIC) for additional computational power, is utilized by both the reconstruction subsystem 80 and the CAD subsystem 100 to provide sufficient computing speed to the object detecting system 10. It should be appreciated, however, that any apparatus capable of computation at high rates may be acceptable. The CAD subsystem 100 works in conjunction with the reconstruction subsystem 80 to differentiate adjacent objects from one another.

Figure 2:
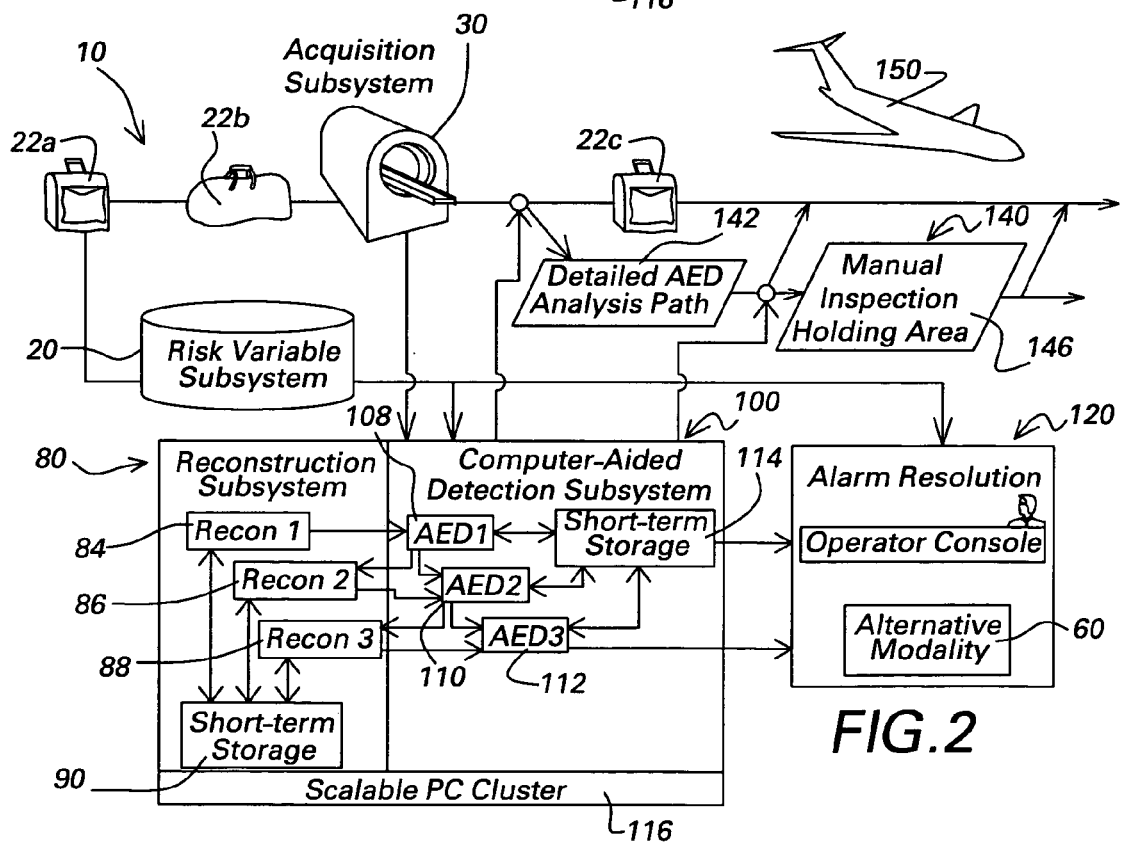
FIG. 2 is a perspective schematic view of one aspect of the object detecting system of FIG. 1.

An aspect of the object detection system is illustrated in FIG. 2. Specifically, an object detection system 10' shown in FIG. 2 differs from the object detection system 10 of FIG. 1 only in the reconstruction subsystem 80' and the CAD subsystem 100'. The reconstruction subsystem 80' includes a plurality of reconstruction stages 84, 86, 88, each of which includes one or more algorithms for reconstructing view data. The CAD subsystem 100' includes AED stages 108, 110, 112. As illustrated in FIG. 2, the reconstruction stage 84 is in communication with the AED stage 108, which in turn is in communication with the short-term storage 114, the AED stage 110, and the reconstruction stage 86. The AED stage 110 is in communication with the AED stage 112, the short-term storage 114, and the reconstruction stage 88. The AED stage 112 is in communication with the short-term storage 114 and the alarm resolution subsystem 120 and the alternative modality subsystem 60.

One or more of the AED stages 108, 110, 112 utilize a differential operator, for example, such as a Hessian tensor, for distinguishing the image data of one object from the image data of another object. A Hessian tensor is a symmetric matrix of partial second derivatives. Local properties of an object can be detected from eigenvalues and eigenvectors, which can be obtained by decomposing the differential operator. A Hessian tensor for a three-dimensional structure is represented in Table 1.

TABLE 1

| $\delta^2 I/\delta x^2$ | $\delta^2 I/\delta x \delta y$ | $\delta^2 I/\delta x \delta z$ |
| $\delta^2 I/\delta y \delta x$ | $\delta^2 I/\delta y^2$ | $\delta^2 I/\delta y \delta z$ |
| $\delta^2 I/\delta z \delta x$ | $\delta^2 I/\delta z \delta y$ | $\delta^2 I/\delta z^2$ |

The eigenvectors of the Hessian tensor represented in Table 1 are illustrated in FIGS. 3–6. These eigenvectors correspond to the principal axes of the partial second derivatives. The eigenvector associated with the largest eigenvalue represents the direction along which the partial second derivative is a maximum. Although a Hessian tensor is described as an example of a differential operator, it should be appreciated that other differential operators may also be used, such as, for example, a Curvature tensor.

Referring specifically to FIG. 3, a cylindrically-shaped object 12 is illustrated showing the eigenvectors $E_1$, $E_2$, $E_3$ associated with the principal axes of the object 12. The eigenvectors $E_1$, $E_2$ represent the direction along which the partial second derivatives are at a maximum. FIG. 4 illustrates a locally sheet-like material 14 with the eigenvectors $E_1$, $E_2$, $E_3$ shown. For the locally sheet-like material 14, the eigenvector $E_1$ represents the direction along which the partial second derivative is at a maximum. FIGS. 5 and 6 illustrate, respectively, a sphere 16 and a blob-like material 18, each with the eigenvectors $E_1$, $E_2$, $E_3$ shown. The eigenvectors $E_1$, $E_2$, $E_3$ for the sphere 16 and for the blob-like material 18 are not aligned along any axis in particular as they do not have principal directions as is the case with the locally cylindrical and sheet-like objects. Table 2 illustrates the relative relationship among eigenvalues for each type of object illustrated in FIGS. 3–6.

TABLE 2

| Eigenvalue | Sphere | Cylinder | Sheet | Bulk |
|---|---|---|---|---|
| $\lambda_1$ | H | H | H | L |
| $\lambda_2$ | H | H | L | L |
| $\lambda_3$ | H | L | L | L |

A review of Table 2 indicates that locally, sheet-like materials have one high (H) eigenvalue ($\lambda_1$) with a counterpart eigenvector $E_1$ (shown in FIG. 4) normal to the surface of the locally sheet-like material 14, and two low (L) eigenvalues ($\lambda_2$, $\lambda_3$) with counterpart eigenvectors $E_2$, $E_3$ that are mutually orthogonal to the first eigenvector $E_1$. High (H) and low (L) are measured with respect to the magnitude of the eigenvalues $\lambda_1$, $\lambda_2$, $\lambda_3$. Objects that are locally sheet-like, such as, for example, a sheet-like explosive material, can be identified using the eigenvalues of the Hessian tensor. Similarly, by combining the eigenvalues in a different manner, functions can be created that respond to objects that are locally cylindrical, spherical, or blob-like.

For the locally sheet-like material 14 of FIG. 4, each of the eigenvalues $\lambda_2$, $\lambda_3$ are approximately zero, which is considerably greater than the magnitude of the eigenvalue $\lambda_1$. Thus, the eigenvalue $\lambda_1$ is high in absolute terms relative to the eigenvalues $\lambda_2$, $\lambda_3$. For the cylinder of FIG. 3, each of the eigenvalues 2, 3 are considerably less than the eigenvalue $\lambda_1$, which is approximately zero. Thus, the eigenvalues $\lambda_2$, $\lambda_3$ are high in absolute terms relative to the eigenvalue $\lambda_1$. For the sphere of FIG. 5, each of the eigenvalues $\lambda_1$, $\lambda_2$, $\lambda_3$ are approximately equal to each other and considerably less than zero, and thus they are all high in relative terms. For the blob-like material of FIG. 6, each of the eigenvalues $\lambda_1$, $\lambda_2$, $\lambda_3$ are approximately equal to each other and considerably more than zero, and thus they are all low in relative terms.

A function that can be used to detect objects that are locally sheet-like, such as the locally sheet-like material 14, may be represented by the equation:

$$F = -\lambda_1 - K^*(abs(\lambda_2) + abs(\lambda_3))$$

where $\lambda_1$ is equal to the value of the eigenvalue with the largest magnitude, K is a user selectable constant, and $\lambda_2$ and $\lambda_3$ are the values of the other two eigenvalues. This algorithm responds more strongly for locally sheet-like materials, such as the locally sheet-like material 14, than for other geometries. The eigenvectors of the Hessian tensor represent the directional change of the surface of the object. For a sheet-like material, the eigenvector corresponding to the largest magnitude eigenvalue represents the normal to the object surface. These eigenvectors are then used to determine if neighboring voxels should be grouped one with another to form a sheet-like material. Then, a classifier can be used to determine if the entire object is a sheet and whether it falls within the parameters of a dangerous object.

Figure 7:
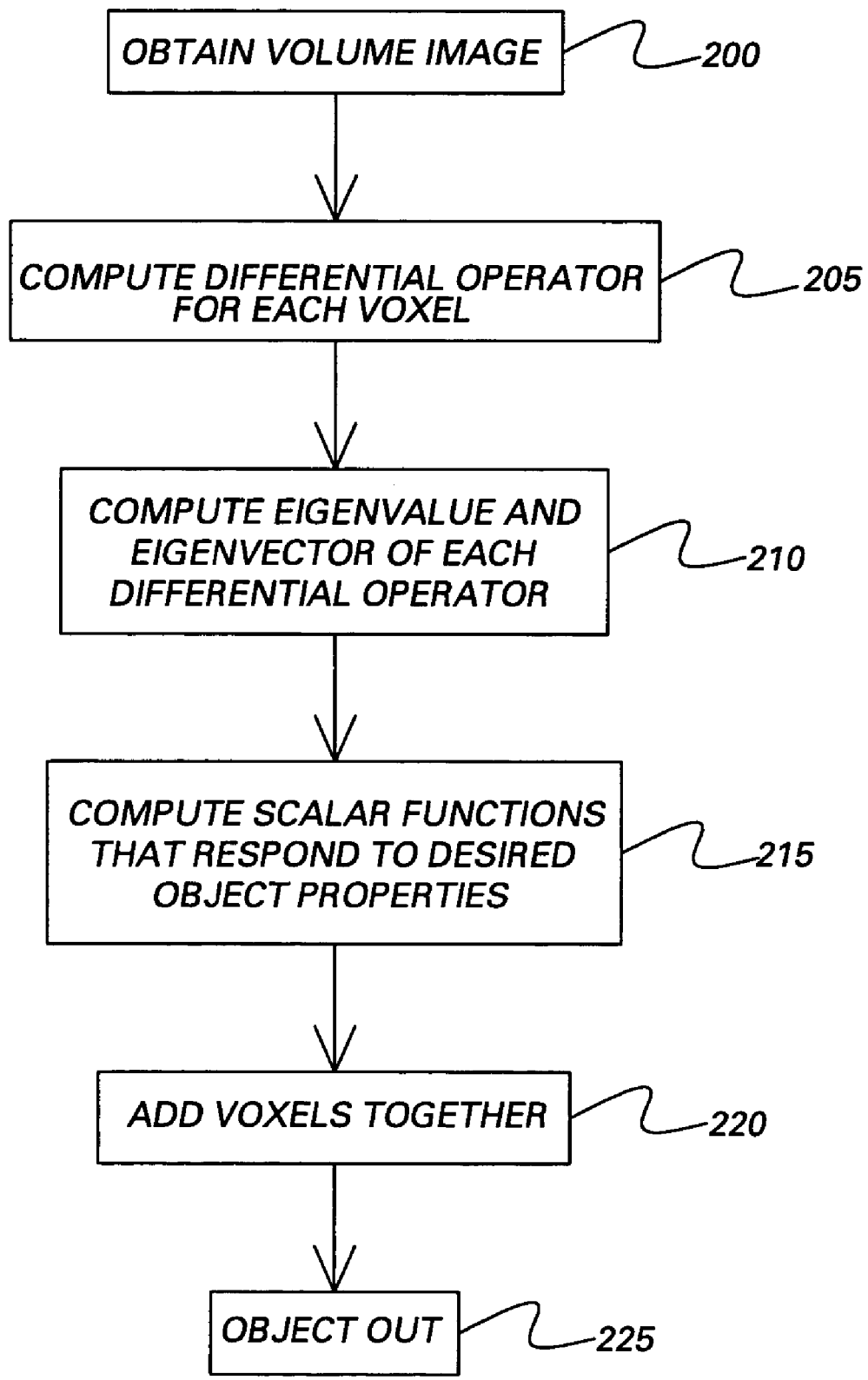
FIG. 7 illustrates an exemplary method for determining the shape of an object in accordance with an embodiment of the invention.

With specific reference to FIG. 7, next will be described a method for identifying an object as locally sheet-like, cylindrical, spherical, or blob-like. At Step 200, a volume image is obtained. The volume image may be obtained through the use of the acquisition subsystem 30 utilizing a CT scanner. For example, an article such as a piece of luggage 22n is transported through a CT scanner of the acquisition subsystem 30, which obtains view data of the luggage 22n. The view data is transmitted to the reconstruction subsystem 80 to be turned into image or volume data.

At Step 205, the differential operator is computed for each voxel obtained in the volume data. Then, at Step 210, the eigenvalues and eigenvectors of each of the Hessian tensors are computed. Scalar functions that respond to desired object properties are then computed at Step 215. For example, if a sheet-like material is being sought, the desired object properties is one large eigenvalue with a corresponding eigenvector normal to the object surface and two smaller eigenvalues with corresponding eigenvectors orthogonal to the eigenvector normal to the object surface. For a locally sheet-like material, the scalar function computed is $$F = -\lambda_1 - K^*(abs(\lambda_2) + abs(\lambda_3)).$$

Next, at Step 220, all of the voxels are added together. Specifically, a scalar function of the eigenvalues is computed to ascertain whether each voxel represents a portion of an object that is locally sheet-like.

The voxels also are checked against other voxels to promote the inclusion of all voxels which respond similarly to the scalar function and are contiguous in three-dimensional space to ensure connected components are included together. For example, for locally sheet-like objects, the eigenvector corresponding to the largest magnitude eigenvalue is normal to the plane of the sheet. When grouping voxels to form an object, only voxels that satisfy both the scalar function of the eigenvalues and have plane normal vectors that are close to their neighbors are grouped into the same structure. For locally cylindrical objects, the eigenvector corresponding to the smallest magnitude eigenvalue gives the axis of the cylinder. Both the scalar function and the vector direction are used to determine whether voxels belong to the same object having a locally cylindrical characteristic.

Finally, at Step 225, a determination is made as to the identity of an object within the luggage 22n. A classifier may be used to identify the object as being dangerous or benign.

For determining the identity of a sheet-like material in luggage 22n, such as the sheet-like material 14 of FIG. 4, the CT scanner takes view data of the luggage 22n, and the view data is reconstructed into three-dimensional image data by the reconstruction subsystem 80 (Step 200). At that point, the Hessian tensor for each of the voxels is determined (Step 205). Then, the local values of each of the voxels are determined (Step 210). A scalar function of eigenvalues is then created that responds to a specific object type (Step 215). These scalar functions of eigenvalues are what will identify an object as being the sheet-like material 14, as opposed to, for example, a cylindrical object or a spherical object. The voxels that correspond to certain qualities representative of a sheet-like material are then added together (Step 220). For example, voxels that have a density (an intensity of voxels) in a particular range, that have a scalar response (a function of the local shape) above a particular threshold (for example, 0.3), and that have vectors that are surface normal close to other voxels having surface normal vectors indicate a sheet-like material. At that point a determination that the object is sheet-like can be made (Step 225).

For determining a blob-like material or a spherical object, the previously described method is used except that the voxels are searched only for a particular density and scalar response. For determining a cylindrical object, the previously described method is used except that the voxels are searched only for a particular scalar response and for axes oriented in the same direction. The previously described method can be used to reject objects that have properties that are inconsistent with the properties being sought.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while exemplary embodiments of the invention have been described in reference to identifying an object within luggage 22n, it should be appreciated that the luggage 22n may be any enclosable container capable of housing one or more objects. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A system for distinguishing a specific object from other objects residing within an enclosed container, comprising:
   an acquisition subsystem for acquiring information pertaining to a specific object;
   a reconstruction subsystem for reconstructing acquired information pertaining to the specific object into image data; and
   a computer-aided detection subsystem adapted for identifying the specific object through differential operators.

2. The system of claim 1, wherein the acquisition subsystem comprises a computed tomography machine.

3. The system of claim 2, wherein the computed tomography machine comprises one from the group consisting of a $3^{rd}$ generation computed tomography scanner, a $4^{th}$ generation computed tomography scanner, a $5^{th}$ generation computed tomography scanner, and a computed tomography scanner including a stationary x-ray source and a stationary detector.

4. The system of claim 1, wherein the computer-aided detection subsystem is configured to identify the specific object as being one from the group consisting of locally sheet-like, spherical, cylindrical, and blob-like.

5. The system of claim 1, wherein the differential operators comprise a Hessian tensor.

6. The system of claim 1, wherein the differential operators comprise a Curvature tensor.

7. The system of claim 1, wherein the computer-aided detection subsystem comprises more than one stage for distinguishing the specific object from the other objects.

8. The system of claim 7, wherein at least one of the more than one stage computes a differential operator for each voxel of the image data.

9. The system of claim 8, wherein at least one of the more than one stage computes eigenvalues and eigenvectors of the differential operators.

10. The system of claim 9, wherein at least one of the more than one stage computes a scalar function of the eigenvalues to ascertain whether each of the voxels of the image data represents a portion of the specific object.

11. The system of claim 10, wherein the scalar function responds to a greater degree to locally sheet-like materials than to materials having other geometries.

12. The system of claim 11, wherein the scalar function is equal to the negative of the largest magnitude eigenvalue minus the product of a user selectable constant times the addition of two additional eigenvalues.

13. A system for distinguishing a specific object from other objects residing within an enclosed container, comprising:
   an acquisition subsystem for acquiring information pertaining to a specific object, wherein the acquisition subsystem comprises a computed tomography machine;
   a reconstruction subsystem for reconstructing acquired information pertaining to the specific object into image data; and
   a computer-aided detection subsystem adapted for identifying the specific object through differential operators, wherein the computer-aided detection subsystem comprises more than one stage.

14. The system of claim 13, wherein the computed tomography machine comprises one from the group consisting of a $3^{rd}$ generation computed tomography scanner, a $4^{th}$ generation computed tomography scanner, a $5^{th}$ generation computed tomography scanner, and a computed tomography scanner including a stationary x-ray source and a stationary detector.

15. The system of claim 13, wherein the computer-aided detection subsystem is configured to identify the specific object as being one from the group consisting of locally sheet-like, spherical, cylindrical, and blob-like.

16. The system of claim 13, wherein the differential operators comprise a Hessian tensor.

17. The system of claim 13, wherein the differential operators comprise a Curvature tensor.

18. The system of claim 13, wherein at least one of the more than one stage computes a differential operator for each voxel of the image data.

19. The system of claim 18, wherein at least one of the more than one stage computes eigenvalues and eigenvectors of the differential operators.

20. The system of claim 19, wherein at least one of the more than one stage computes a scalar function of the eigenvalues to ascertain whether each of the voxels of the image data represents a portion of the specific object.

21. The system of claim 20, wherein the scalar function responds to a greater degree to locally sheet-like materials than to materials having other geometries.

22. The system of claim 21, wherein the scalar function is equal to the negative of the largest magnitude eigenvalue minus the product of a user selectable constant times the addition the two additional eigenvalues.

23. A system for identifying a specific object from other objects resident within an enclosed container, comprising:
   an acquisition subsystem for acquiring information pertaining to a specific object;
   a reconstruction subsystem for reconstructing acquired information pertaining to the specific object into image data; and
   a means for identifying the specific object through the use of differential operators, wherein vectors derived from the differential operators are used in the identification of the specific object.

24. The system of claim 23, wherein the acquisition subsystem comprises a computed tomography machine from the group consisting of a $3^{rd}$ generation computed tomography scanner, a $4^{th}$ generation computed tomography scanner, a $5^{th}$ generation computed tomography scanner, and a computed tomography scanner including a stationary x-ray source and a stationary detector.

25. The system of claim 23, wherein the means for identifying the specific object through the use of differential operators comprises a computer-aided detection subsystem configured to identify the specific object as being one from the group consisting of locally sheet-like, spherical, cylindrical, and blob-like.

26. The system of claim 25, wherein the computer-aided detection subsystem comprises more than one stage for distinguishing the specific object from the other objects.

27. The system of claim 26, wherein at least one of the more than one stage computes eigenvalues and eigenvectors of the differential operators.

28. The system of claim 27, wherein at least one of the more than one stage computes a scalar function of the eigenvalues to ascertain whether each of the voxels of the image data represents a portion of the specific object.

29. The system of claim 23, wherein the differential operators comprise a Hessian tensor.

30. The system of claim 23, wherein the differential operators comprise a Curvature tensor.

31. A method for distinguishing a specific object from other objects within an enclosed container, comprising the steps of:
   obtaining image data of a specific object;
   computing a differential operator for each voxel of the image data;
   computing eigenvalues and eigenvectors for each of the voxels; and
   computing a scalar function of the eigenvalues to ascertain whether each of the voxels represents a portion of the specific object.

32. The method of claim 31, wherein said obtaining step comprises:
   acquiring information pertaining to the specific object; and
   reconstructing the acquired information pertaining to the specific object into image data.

33. The method of claim 32, wherein said acquiring step comprises acquiring information through a computed tomography machine.

34. The method of claim 31, wherein the computing a differential operator step comprises computing a differential operator for each voxel of the image data with at least one stage of a computer-aided detection subsystem.

35. The method of claim 34, wherein the computing eigenvalues and eigenvectors step comprises computing eigenvalues and eigenvectors of the differential operators with the at least one stage.

36. The method of claim 31, wherein the computing a differential operator step comprises computing a Hessian tensor.

37. The method of claim 31, wherein the computing a differential operator step comprises computing a Curvature tensor.

38. The method of claim 31, wherein the scalar function responds to a greater degree to locally sheet-like materials than to materials having other geometries.

39. The method of claim 31, further comprising identifying the one object as being from the group of objects consisting of locally sheet-like, spherical, cylindrical, and blob-like objects.

40. A method for distinguishing one locally sheet-like object from other objects within an enclosed container, comprising the steps of:
   obtaining image data of a locally sheet-like object;
   computing a differential operator for each voxel of the image data with at least one stage of a computer-aided detection subsystem;
   computing eigenvalues and eigenvectors for each of the voxels; and
   computing a scalar function of the eigenvalues to ascertain whether each of the voxels represents a portion of the locally sheet-like object;
   wherein the scalar function responds to a greater degree to locally sheet-like materials than to materials having other geometries.

41. The method of claim 40, wherein said obtaining step comprises:
   acquiring information pertaining to the one object; and
   reconstructing the acquired information pertaining to the one object into image data.

42. The method of claim 41, wherein said acquiring step comprises acquiring information through a computed tomography machine.

43. The method of claim 40, wherein the computing eigenvalues and eigenvectors step comprises computing eigenvalues and eigenvectors of each differential operator with the at least one stage.

44. The method of claim 40, wherein the computing a differential operator step comprises computing a Hessian tensor.

45. The method of claim 40, wherein the computing a differential operator step comprises computing a Curvature tensor.

* * * * *